United States Patent
Pflug et al.

(10) Patent No.: US 11,583,682 B2
(45) Date of Patent: Feb. 21, 2023

(54) ANTENNA FOR AN IMPLANTABLE PULSE GENERATOR

(71) Applicant: ONWARD MEDICAL N.V., Eindhoven (NL)

(72) Inventors: Hans Pflug, Eindhoven (NL); Jeroen Tol, Eindhoven (NL); Koen Weijand, Eindhoven (NL)

(73) Assignee: Onward Medical N.V., Eindhoven (NL)

( * ) Notice: Subject to any disclaimer, the term of this patent is extended or adjusted under 35 U.S.C. 154(b) by 15 days.

(21) Appl. No.: 17/113,661

(22) Filed: Dec. 7, 2020

(65) Prior Publication Data

US 2022/0176132 A1 Jun. 9, 2022

(51) Int. Cl.
*A61N 1/372* (2006.01)
*A61N 1/375* (2006.01)

(52) U.S. Cl.
CPC .......... *A61N 1/37211* (2013.01); *A61N 1/375* (2013.01); *A61N 1/3754* (2013.01); *A61N 1/37229* (2013.01)

(58) Field of Classification Search
CPC ............ A61N 1/37211; A61N 1/37229; A61N 1/375; A61N 1/3754
See application file for complete search history.

(56) References Cited

U.S. PATENT DOCUMENTS

| | | | | |
|---|---|---|---|---|
| 6,115,634 A | * | 9/2000 | Donders | A61N 1/37512 607/32 |
| 7,813,809 B2 | | 10/2010 | Strother et al. | |
| RE45,030 E | * | 7/2014 | Stevenson | A61B 90/90 343/873 |
| 2005/0075693 A1 | * | 4/2005 | Toy | A61N 1/37211 607/60 |
| 2013/0150915 A1 | * | 6/2013 | Kane | A61N 1/37512 607/36 |
| 2015/0012061 A1 | * | 1/2015 | Chen | A61N 1/3787 607/59 |
| 2015/0094791 A1 | * | 4/2015 | Edgell | G09F 3/10 101/483 |
| 2016/0144167 A1 | * | 5/2016 | Bakker | A61B 5/06 607/63 |
| 2017/0361115 A1 | * | 12/2017 | Aghassian | A61N 1/36142 |
| 2018/0280706 A1 | * | 10/2018 | Maile | H02J 7/00034 |

FOREIGN PATENT DOCUMENTS

| | | | |
|---|---|---|---|
| EP | 1575665 A1 | 6/2004 | |
| EP | 1680182 A1 | 4/2005 | |
| EP | 1675648 A1 | 5/2005 | |
| EP | 2868343 A1 | 6/2015 | |
| WO | WO-2020028088 A1 * | 2/2020 | .............. H02M 3/00 |

* cited by examiner

*Primary Examiner* — Catherine M Voorhees
(74) *Attorney, Agent, or Firm* — Finnegan, Henderson, Farabow, Garrett & Dunner, LLP.

(57) ABSTRACT

An antenna for an implantable medical device, the antenna being configured for inductive wireless power transfer and/or near-field magnetic induction communication, the antenna comprising at least one coil or at least one set of coils, each coil comprising several windings. Furthermore, the present disclosure relates to an implantable medical device (IMD).

20 Claims, 4 Drawing Sheets

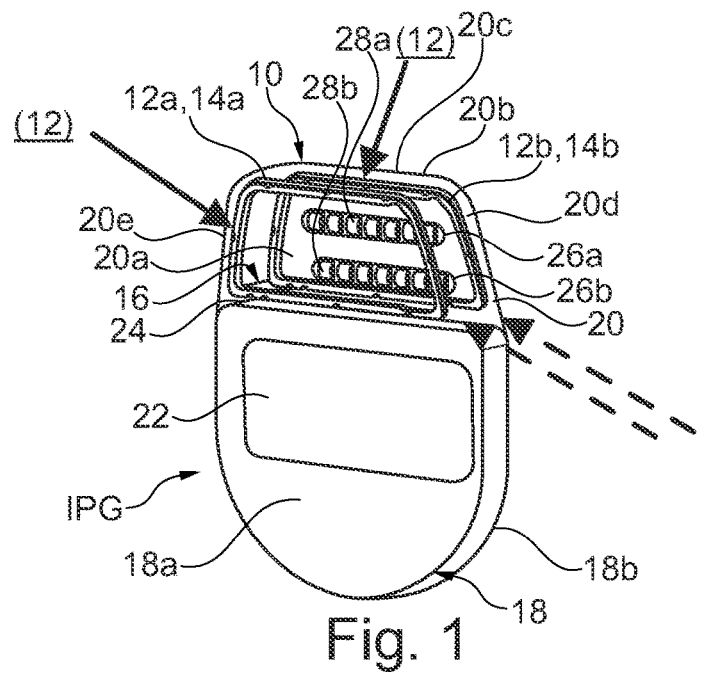
Fig. 1
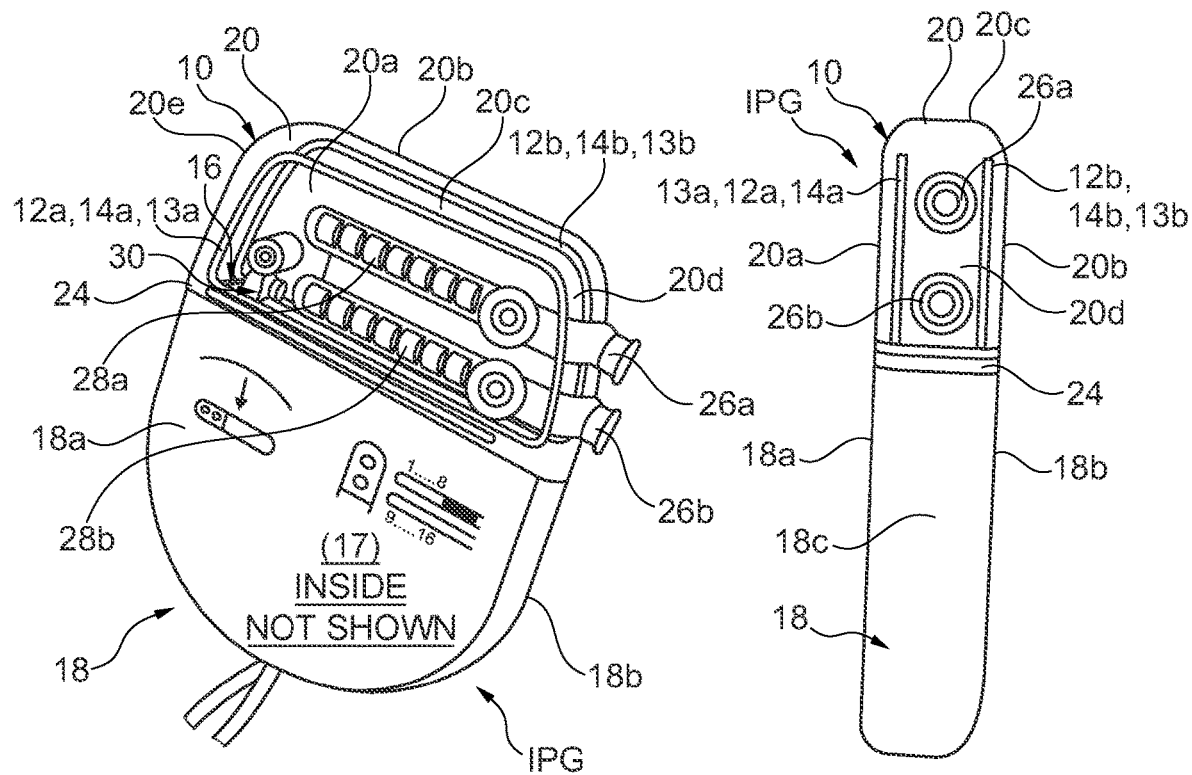
Fig. 2a
Fig. 2b

ANTENNA FOR AN IMPLANTABLE PULSE GENERATOR

TECHNICAL FIELD

Disclosed embodiments relate to an antenna for a medical device, especially an implantable medical device (IMD), in some embodiments a pulse generating system, in some embodiments an implantable pulse generating system, in some embodiments for a communication and powering system of a pulse generating system. The present disclosure further relates to an IMD.

BACKGROUND AND SUMMARY

Pulse generating systems are implemented in various medical applications, inter alia pacemakers and neuromodulation applications, such as neuromodulation for the treatment of a subject, e.g. in the field of improving recovery after neurological disorders such as spinal cord injury and/or stroke.

In particular, such pulse generation systems may be implantable pulse generating systems and are used in systems to deliver adaptive electrical spinal cord stimulation to facilitate and restore locomotion after neuromotor impairment as e.g. described in EP 2 868 343 A1.

U.S. Pat. No. 7,813,809 B2 describes an implantable pulse generator (IPG) for prosthetic or therapeutic stimulation of muscles, nerves, or central nervous system tissue, or any combination, sized and configured to be implanted in subcutaneous tissue. The IPG includes a case and a control circuitry located within the case, and includes a primary cell or rechargeable power source, a receive coil for receiving an RF magnetic field to recharge the rechargeable power source, non-inductive wireless telemetry circuitry, and a microcontroller for control of the IPG.

Communication and power charging systems in a medical field may be used to submit energy and communication signals transcutaneously, in particular between a non-implanted device and an IPG.

For example, US 2015/0012061 A1 relates to a medical device for providing a stimulation therapy including a coil configured to receive both inductive charging and telemetry signals. The inductive charging signals are in a first frequency band. The telemetry signals are in a second frequency band higher than the first frequency band. The medical device includes inductive charging circuitry configured to provide electrical power to the medical device via the inductive charging signals. The medical device includes telemetry circuitry configured to conduct telecommunications with a external device via the telemetric signals. The medical device includes a first component electrically coupled between the coil and the inductive charging circuitry. The first component is configured to allow the inductive charging signals to pass through. The medical device includes a second component electrically coupled between the coil and the telemetric circuitry. The second component is configured to substantially block the inductive charging signals while allowing telemetric signals to pass through.

Alternative solutions are for example disclosed by EP 1 680 182 A1, EP 1 675 648 A1 and EP 1 575 665 A1.

Of note, IPG coils may be attached to the exterior of the housing of the IPG or placed in the housing, in particular the main housing. The first approach results in a larger size of the IPG in terms of its largest width and thus is an adverse option, as the larger the size of the IPG is, the worse it is for the patient. The second approach is also an adverse option due to the conducting properties of the usually used titanium housing. A conductive housing restricts the usable frequency band of inductive charging and communication signals, and consequently, the charging performance, e.g. maximum IPG charging current and charging distance to a non-implantable charging device, and communication band options.

The coil could be placed in an IPG header which may be made of non-conducting material and attached to the IPG housing or IPG main housing. This represents a practical solution of integrating a coil into an IPG, both in terms of form factor of the IPG and in terms of IPG charging and communication performance.

However, as far as charging is concerned, this introduces the risk of implanting the IPG with the side of the header containing the coil not closest to the skin of a patient if a common a-symmetric header coil design is used, effectively increasing the implantation depth of the IPG header coil. This may adversely increase the implantation depth of the header coil by half the header thickness and thus may reduce the performance of the wireless charging link. In other words, the distance between the IPG (header) coil and the coil of the related non-implanted device sending signals to the IPG is not optimal.

It is an object of the present disclosure to improve an antenna and/or an induction coil of an IPG of a neuromodulation and/or neurostimulation system, in particular in that a better performance of the IPG in terms of increasing a coupling coefficient or coupling factor of an inductive wireless link and therefore the neuromodulation and/or neurostimulation system is enabled.

This object is solved according to the present disclosure with an antenna with the features of claim 1 and the features described herein. Accordingly, an antenna for an implantable medical device (IMD), the antenna being configured for inductive wireless power transfer and/or near-field magnetic induction (NFMI) communication, the antenna comprising at least one coil or at least one set of coils, each coil comprising several windings.

The disclosure provides that, by designing an antenna for an IMD, e.g. an IPG, e.g. an IPG for neuromodulation and/or neurostimulation, comprising at least one coil or one set of coils, each coil comprising several windings, one may avoid that the distance between coil and skin of a patient implanted with the IMD is not minimal. Thus, it does not matter which side of the IMD, e.g. which side of an IPG, faces the skin of the patient and thus is closer to the related non-implanted device. In other words, the features of the antenna according to the present disclosure may enable placing the antenna in minimal distance to the skin of the patient, independent of its orientation, thus in minimal distance for inductive wireless power transfer and/or near field magnetic induction (NFMI) communication. The antenna design is therefore optimized for transferring a required amount of power from a non-implanted device to the IMD, in particular to an IMD battery charging circuit to charge the battery. Further, the antenna design may be optimal for communication between a non-implanted device and the IMD (bidirectionally, using NFMI). Overall, the antenna design may enable better charging and/or communication performance of the IMD and optimized neuromodulation/neurostimulation.

In general, the IMD may be an active medical device, a pacemaker, a monitoring device, a drug administration device or an IPG, in some embodiments a cochlear implant, a diaphragm stimulator, a sphincter stimulator, a bladder stimulator, and/or a neurostimulator and/or neuromodulator.

A set of coils may be or may comprise at least two coils. However, any number of coils more than two may be generally possible.

Each coil may be at least partially made of wire, in some embodiments made of gold wire. A coil made of gold wire may have the advantage that it is relatively unsusceptible to corrosion.

In some embodiments, the wire may have a diameter of 0.05 mm to 0.5 mm. The thickness of the wire may be adjusted to the self-guiding behavior of the wire. Due to the self-guiding behavior of the wire, it may be possible that the wire guide can also run continuously during orthocyclic winding and does not need to follow step by step.

In some embodiments, the inductive wireless power transfer may be a resonant inductive wireless power transfer.

Further, the at least one coil or the coils of the at least one set of coils each may form a rectangular form, especially a trapezoidal form. Beyond the number of windings, the inductance of a coil also results from the dimension of a coil. Given that the housing of IMDs, e.g. IPGs, or certain parts of IMDs, e.g. certain parts of IPGs, such as a header, are often characterized by a rectangular form, especially a trapezoidal form, the coil or the coils of the at least one set of coils forming a rectangular form, especially a trapezoidal form, may enable maximum use of the dimension of the housing of the IMD, e.g. of the IPG. Thus, using coils each forming a rectangular form, especially a trapezoidal form, may enable a maximum level of inductance relative to the given dimensions of the housing of the IMD, e.g. of the IPG.

Further, the coils of the at least one set of coils may be connected by means of at least one bridging element. This connection between the coils of the at least one set of coils may enable that the inductance of a first coil may be combined with the inductance of a second coil. In other words, the current flowing in one coil may induce a voltage in the adjacent, second coil, finally causing an increased mutual inductance of the coils of the at least one set of coils.

According to the present disclosure, an IMD comprising at least one antenna as described above is disclosed, especially an IPG comprising at least one antenna as described above is disclosed.

In some embodiments, the IMD may have a main housing part and a header part attached to the main housing part, wherein the at least one antenna may be arranged in the header part. As mentioned above, this arrangement may result in a practical solution of integrating a coil into an IMD, in terms of form factor of the IMD, available assembly space and in terms of performance of the IMD.

An IMD antenna and/or coil may be used for 5-8 MHz, especially 6.78 MHz, inductive wireless power transfer, e.g. resonant inductive wireless power transfer, and 8-12 MHz, especially 10.6 MHz, NFMI communication. Arranging the antenna in the metal housing of an IMD, such as titanium, may be disadvantageous when using the antenna and/or coil for 5-8 MHz, especially 6.78 MHz, inductive wireless power transfer, e.g. resonant inductive wireless power transfer, and 8-12 MHz, especially 10.6 MHz, near field magnetic induction communication, due to the conducting properties of the housing leading to eddy-current losses and severe signal attenuation. Thus, arranging the IMD antenna and/or coil inside the titanium housing part of the IMD may be not desirable. Further, arranging the antenna around the housing of the IMD may be disadvantageous and not desirable as this may result in a larger size of the IMD in terms of its largest width while at the same time adding cumbersome manufacturing steps to the IMD production. Arranging the antenna in the header part may overcome these disadvantages.

Further, the header part may be transparent. By using a transparent header part, it may be enabled that the integrity of the coils may be checked visually at the end of IMD production, e.g. for quality control reasons.

In some embodiments, the header part may be at least partially made of a polymer such as but not limited to epoxy, polyurethane and/or silicone. In some embodiments, the header part may be made of medical grade material. In some embodiments, the header may be at least partially made of a medical grade polymer such as but not limited to medical grade epoxy, medical grade polyurethane and/or medical grade silicone. Alternatively, and/or additionally, the header part may be made of medical grade polyamide and/or medical grade polypropylene. As the header may be made of non-conductive material it may not support or function as an indifferent electrode due to eddy-current losses, leading to better performance of the IMD.

Further, the header may be at least partially made of a polymer such as but not limited to epoxy, polyurethane and/or silicone may have insulation effects.

The coils of the at least one set of coils may be arranged in parallel (in a geometrical sense—electrically arranged in series or may also be arranged electrically in parallel). In some embodiments, arranging a first coil comprising several windings and a second coil comprising several windings in parallel may enable maximal total (mutual) inductance. The geometrical parallel arrangement may be beneficial for the charging function.

Alternatively, the coils of the at least one set of coils each comprising several windings may be arranged orthogonally to each other (in a geometrical sense).

Alternatively, the sets of windings can be arranged orthogonally to each other.

Further, the antenna may comprise at least one further coil or at least one further set of coils. In some embodiments, the at least one further coil or at least one further set of coils may increase the coupling factor between the antenna of the implanted IMD and an antenna and/or coil of a non-implanted device which may charge the IMD battery or communicate with the IMD for controlling reasons.

In some embodiments, the antenna may comprise at least one further coil or at least one further set of coils, wherein the at least one further coil or one further set of coils may be arranged substantially orthogonally with regard to the at least one set of coils, i.e. the first set of coils.

During communication, the non-implanted device may be in a non-optimal orientation with regard to the at least one coil or the coils of the at least one set of coils each comprising several windings arranged in parallel geometrically, resulting in a low coupling factor, e.g. coupling factor null. By introducing at least one further coil or at least one further set of coils comprising several windings, especially substantially orthogonally with regard to the at least one coil or at least one set of coils each comprising several windings, e.g. in an IPG header, communication quality and performance may be improved for these non-optimal orientations without impacting the charging performance much.

Alternatively, the at least one further coil or the at least one further set of coils may be arranged substantially parallelly with regard to the at least one set of coils.

Alternatively, the at least one further coil or the at least one further set of coils may be arranged substantially at an acute or obtuse angle with regard to the at least one set of coils.

If windings are geometrically arranged rectangularly or substantially rectangularly, this can be used to the so-called nulls in case of NFMI use.

Further, the header part of the IMD, e.g. IPG, may comprise a mechanical support structure comprising at least one channel structure in which each winding of a coil is received and wound around the support structure. The mechanical support structure may enable forming and keeping the form of the at least one coil or the coils of the at least one set of coils, such as a rectangular, especially a trapezoidal form. The mechanical support structure may additionally and/or alternatively enable keeping one coil apart from another coil.

The IMD, e.g. the IPG, may comprise connector slots being arranged at least partially within the at least one antenna.

Generally, an IMD header, e.g. an IPG header, may include one or more connector-slots and housing feedthroughs, typically located in the center of the housing-side. Mounting the connectors in the header center may make the header construction easier. According to the present disclosure, this construction advantage may be maintained with the connector slots being arranged at least partially within the at least one antenna.

Further, the connection of the connector slots with the housing-feedthroughs may be more cumbersome in case the connectors are placed more towards one side of the header (outside of its center). This may require bending of the connector connections towards the feedthroughs, therefore requiring more header height and/or width. Therefore, placing the connectors at least partially within the at least one antenna, e.g. in the middle of the antenna, and having the antenna next to the connectors on both sides may lead to a lower volume claim of the antenna in the header and/or the header itself.

Further, the IMD may be or may comprise a switch interface which may decide which of the coils and/or set of coils to use, wherein each coil and/or set of coils comprises its own feed-through and/or is connected to at least one feed-through assigned to the coil. This means that each coil has its own feed-through. This feed-through can be only assigned to this coil and directly connected to it. It is possible that this feed-through is not connected to another coil (directly). In some embodiments, electronics inside the IMD may enable to decide which coil and/or set of coils to use, for example based on a received signal strength (e.g. NFMI signal strength) or charge current strength (charging current magnitude). In some embodiments, this may increase the degree of freedom on electronic functionality, as the antenna configuration may be changed according to the situation.

It is to be understood that both the foregoing general description and the following detailed description are exemplary and explanatory only and are not restrictive of the disclosed embodiments or the scope of the inventions as claimed. The concepts in this application may be employed in other embodiments without departing from the scope of the inventions.

BRIEF DESCRIPTION OF THE FIGURES

Further details and advantages of the disclosed embodiments shall now be disclosed in connection with the drawings. The accompanying drawings, which are incorporated in and constitute a part of this specification, illustrate several embodiments consistent with the disclosure and together with the description, serve to explain the principles of the disclosure.

FIG. 1 shows a schematic perspective view of a first embodiment of an antenna together with an implantable pulse generator according to the present disclosure;

FIG. 2a shows a schematic top view of the first embodiment of the antenna together with the implantable pulse generator according to FIG. 1 in more/greater detail;

FIG. 2b shows a schematic side view of the first embodiment of the antenna together with the implantable pulse generator according to FIG. 1 in more/greater detail;

DETAILED DESCRIPTION

Figure 3A:
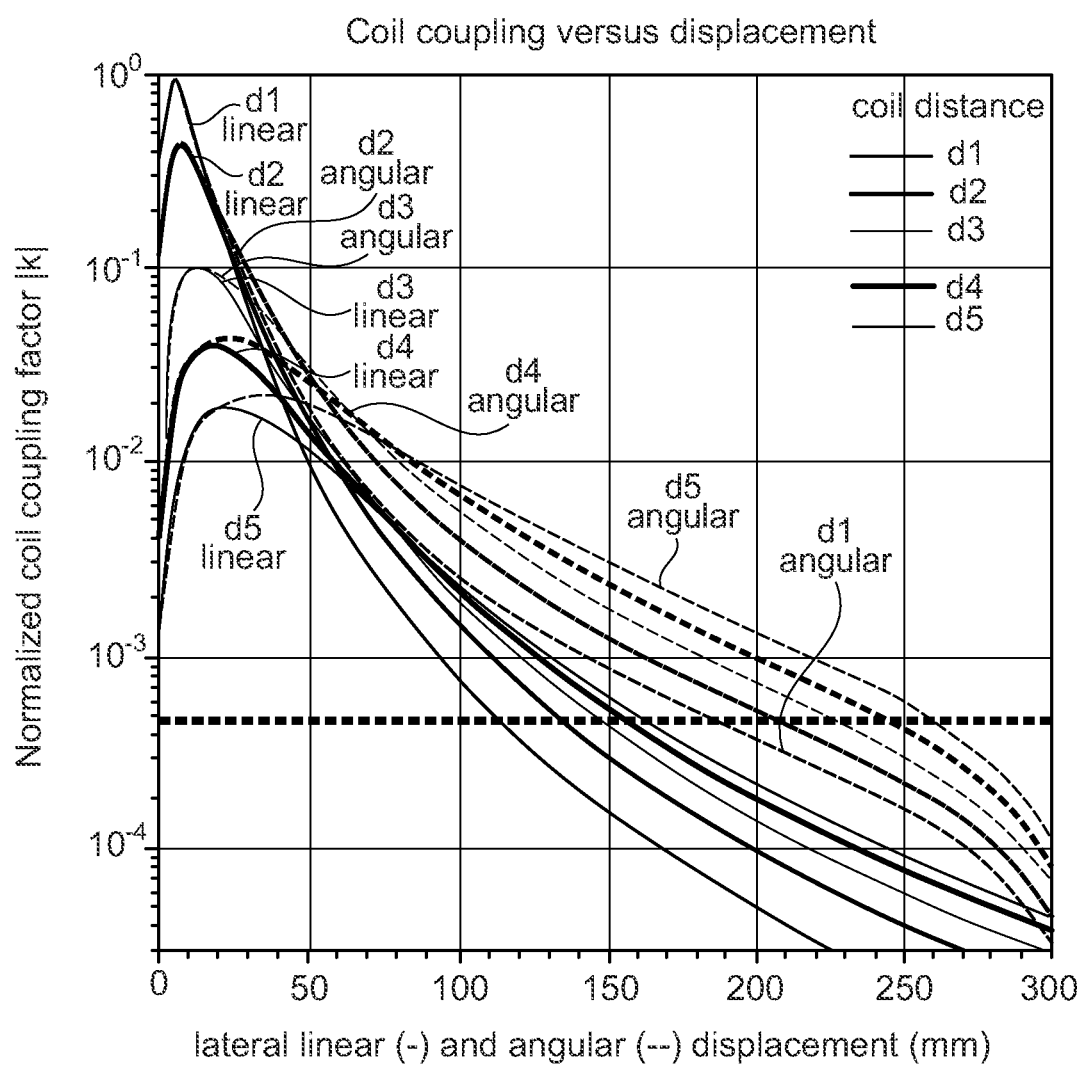
FIG. 3a shows a diagram of a coil coupling coefficient between the implanted IPG coil and the non-implanted device coil of the implanted antenna of the implantable pulse generator according to FIG. 1.

Reference will now be made in detail to exemplary embodiments, discussed with regards to the accompanying drawings. In some instances, the same reference numbers will be used throughout the drawings and the following description to refer to the same or like parts. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

FIG. 1 shows a schematic perspective view of a first embodiment of an antenna 10 together with an implantable pulse generator IPG according to the present disclosure. In this embodiment, an antenna for an implantable medical device IMD is shown. The antenna 10 comprises a set of coils 12a, 12b, wherein each coil 12a, 12b comprises several windings 14a, 14b, respectively. In some embodiments, the antenna 10 comprises two coils 12a, 12b. In this embodiment, the coils 12a, 12b comprise an identical number of windings 14a, 14b. The number of windings 14a, 14b of each coil 12a, 12b may be four.

According to a further embodiment, the number of windings 14a, 14b of each coil 12a, 12b is an integer being bigger or smaller than four. Generally, the number of windings 14a, 14b may be chosen from the range of 1-10 windings 14a, 14b. In one alternative embodiment, the number of windings 14a, 14b of each coil 12a, 12b is two.

The coils 12a, 12b form an induction-coil having an overall number of eight windings 14a, 14b (or so-called turns). Thus, the coils 12a, 12b are electrically connected by means of a bridging element 16. In general, the connection between the coils 12a, 12b is not necessarily an electric connection. In other words, the coils 12a, 12b could be connected by means of a bridging element 16. In an alternative embodiment, the coils 12a, 12b could be connected by means of more than one bridging element 16.

Each of the two coils 12a, 12b form a rectangular form. Especially in the shown embodiment, each of the two coils 12a, 12b form a trapezoidal form. As shown, the windings 14a, 14b are arranged in term of geometry in parallel. As shown, the coils 12a, 12b of the at least one set of coils 12a, 12b are arranged in parallel.

Further, FIG. 1 shows an implantable pulse generator IPG comprising the antenna 10 as mentioned above. In other words, in this embodiment, the implantable medical device IMD may be an implantable pulse generator IPG. The implantable pulse generator IPG has a main housing part 18. The main housing part 18 is formed of a medical-grade metal alloy such as titanium alloys Ti-6Al-4V-ELI or TAV-ELI.

The main housing part 18 includes a thin-walled and shell-like housing structure which surrounds the inner components of the implantable pulse generator IPG in a fluid tight sealed manner.

The inner components can include the battery 22 and the control electronics (not shown in FIG. 1) coupled thereto for generating specific stimulation patterns for neuromodulation, especially neurostimulation, after spinal cord injuries and/or stroke as known in the prior art.

On the top face (based on an implanted condition/orientation) of the main housing part 18, which is arranged opposite to its bottom, a header part 20 is attached to the main housing part 18. According to FIG. 1, the antenna 10 is arranged in the header part 20. At the top face of the main housing part 18, this main housing part 18 and the header part 20 form, at a corresponding sealing face, a further fluid tight sealing with an elastomeric O-Ring 24 having a rectangular shape. The header part 20 has a substantially trapezoidal form. The header part 20 consists of a first and second main surface 20a, 20b (each with the biggest surface area of the header part 20) arranged in parallel.

Further, the first and second main surface 20a, 20b flush with the two planar outer surfaces 18a, 18b of the main housing part 18 being also arranged in parallel with regard to each other. The header part 20 further comprises one header part top surface 20c being orientated opposite of the joint sealing face formed by the main housing part 18 and the header part 20. The header part 20 also comprises two side surfaces 20d, 20e extending between the sealing face and the header part top surface 20c on the one hand.

On the other hand, these two side surfaces 20d, 20e also extend between the two main surfaces 20a, 20b.

The two coils 12a, 12b are arranged at the first and second main surfaces 20a, 20b of the header part 20. Consequently, the two coils 12a, 12b form a symmetrical arrangement within the header part 20 (as indicated by the two parallel, dashed arrows). Especially, the two coils 12a, 12b form a parallel arrangement within the header part 20.

In some embodiments (not shown in FIG. 1), there could be at least one further coil 12 and/or at least one further set of coils 12.

In some embodiments (not shown in FIG. 1), there could be a third coil 12 and/or a fourth coil 12.

The two further arrows of FIG. 1 (continuous lines) indicate further optional locations of an additional third and/or fourth coil 12. The third coil 12 could be arranged at one side surface 20d, 20e. Alternatively, the third coil 12 could be arranged at both side surfaces 20d, 20e. Additionally, or alternatively, the fourth coil 12 could be arranged at the header part top surface 20c. These additional third and fourth coils 12 may each have a substantially orthogonal orientation with respect to the first and second coil 12a, 12b. Alternatively, the third or fourth coil 12 may have a substantially orthogonal orientation with respect to the first or the second coil 12a, 12b.

In other words, the antenna could generally comprise at least one further coil 12, wherein the at least one further coil 12 could be arranged substantially orthogonally with regard to the at least one set of coils 12a, 12b.

Not shown in FIG. 1 is that the third and/or fourth coil 12 is/are built up in the same manner as the first and second coil 12a, 12b.

Some embodiments may implement the use of a different number of windings/turns 14, 14a, 14b for each coil 12, 12a, 12b, for example, to implement a weighing factor between the different orthogonal orientations.

Alternatively, the at least one further coil 12 or the at least one further set of coils 12 could be arranged substantially parallelly with regard to the at least one set of coils 12.

Alternatively, the at least one further coil 12 or the at least one further set of coils 12 could be arranged substantially at an acute or obtuse angle with regard to the at least one set of coils 12.

Generally, the at least one winding 14 of a further coil 12 could be referred to as at least one additional winding 14. This additional at least one winding 14 improves the coil 12, 12a, 12b coupling between the non-implanted external device (not shown in FIG. 1) and the implantable pulse generator IPG in case of a non-optimal orientation between the external device and the implantable pulse generator IPG, especially for NFMI communication.

As can be further depicted from FIG. 1, the header part 20 is transparent. Not directly shown FIG. 1 is that the header part 20 is at least partially made of polymer. In this embodiment, the header part 20 is fully made of polymer. In this embodiment, the polymer is epoxy. In an alternative embodiment, the polymer may be but not limited to epoxy, polyurethane and/or silicone. In general, the polymer may be but not limited to a medical grade epoxy, medical grade polyurethane and/or medical grade silicone. Alternatively, and/or additionally, the header part may be made of medical grade plastic such as medical grade polyamide or medical grade polypropylene.

Not shown in FIG. 1 is that the coils 12, 12a, 12b are made of wire. Not shown in FIG. 1 is that the coils 12, 12a, 12b are made of gold wire. Generally, each coil 12, 12a, 12b can be at least partially made of wire, in some embodiments gold wire. Not shown in FIG. 1 is that the wire has a has a diameter of 0.05 mm to 0.5 mm.

Not shown in FIG. 1 is that the implantable pulse generator IPG could in an alternative embodiment be any other type of implantable medical device IMD. Not shown in FIG. 1 is that the IMD, in some embodiments the IPG, comprises an (electronic) switch interface 17 which decides which of the coils 12, 12a, 12b and/or set of coils 12, 12a, 12b to use, wherein each coil 12, 12a, 12b and/or set of coils 12, 12a, 12b comprises its own feed-through and/or is connected to at least one feed-through assigned to the coil.

Figure 4:
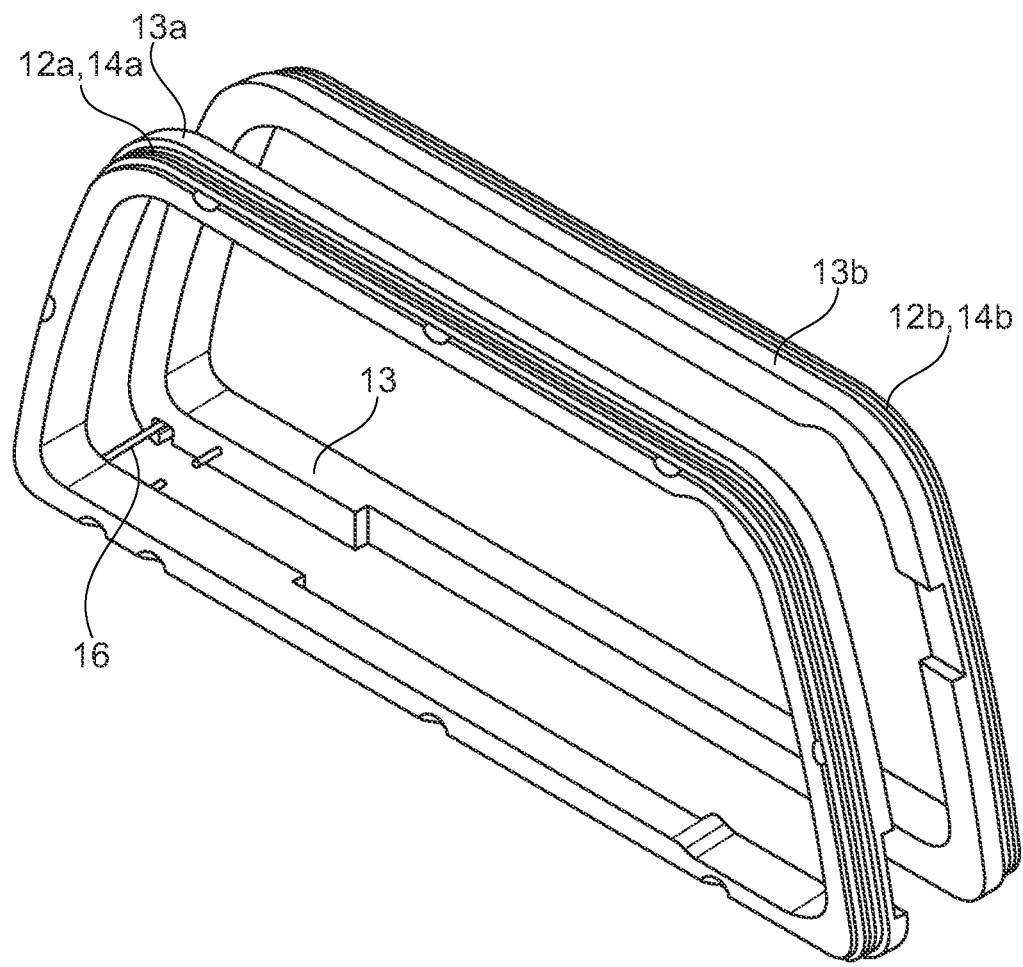
FIG. 4 shows a schematic view of a mechanical support structure comprised in the header part of the IPG disclosed in FIG. 1.

Not shown in FIG. 1 is that the header part 20 (also) comprises a mechanical support structure 13, cf. FIG. 4. The mechanical support structure 13 has a rectangular form, in some embodiments a trapezoidal form. The mechanical support structure 13 is made of non-conductive material. In this embodiment, the mechanical support structure 13 is made of plastic. In this embodiment, the mechanical support structure 13 comprises two channel structures 13a, 13b. In this embodiment, the two channel structures 13a, 13b are separated from each other. The mechanical support structure 13 is carrying the two coils 12a, 12b. In some embodiments, the channel structure 13a is carrying coil 12a. In some embodiments, the channel structure 13b is carrying coil 12b. In other words, each channel structure 13a, 13b is configured to carry one coil 12a, 12b. The mechanical support structure 13 is carrying the windings 14a, 14b. In some embodiments, the channel structure 13a is carrying the windings 14a. In some embodiments, the channel structure 13b is carrying the windings 14b. In general, the mechanical support structure 13 forms the form of the coils 12a, 12b.

In general, the header part 20 comprises a mechanical support structure 13 comprising at least one channel structure 13a, 13b in which each winding 14a, 14b of a coil 12a, 12b is received and wound around the support structure 13.

FIG. 2a shows a schematic top view of the first embodiment of the antenna 10 together with the implantable pulse generator IPG according to FIG. 1 in more detail. Especially, the two coils 12a, 12b are arranged at the edges of the first and second main surfaces 20a, 20b of the header part 20. For example, the two coils 12a, 12b of the windings 14a, 14b are arranged at the edges of the first and second main surfaces 20a, 20b of the header part 20 by embedding them therein. The embedding can be done as here for example shown by overmolding. Alternatively, and/or additionally, injection molding may be implemented. Further, the optional third and/or fourth coils is/are integrated in the side and header part top surface(s) 20c, 20d, 20e in the same manner as described for the main surfaces 20a, 20b.

As can be depicted in greater detail in FIG. 2a, the two coils 12a, 12b are connected by a bridging element 16. The bridging element 16 may be optionally also used for further connection of the third and/or fourth coil 12. In an alternative embodiment (not shown), all coils 12, 12a, 12b may be equipped with their own feed-through connections and these coils may be electronically connected, i.e. via a connection matrix, in a desired configuration depending on e.g. received charge current or received NFMI signal strength. This bridging element 16 is also embedded within the header part 20 and extends between the two coils 12a, 12b at one or both side surfaces 20d, 20e.

As can be further depicted from FIG. 2a, the implantable pulse generator IPG, at its header part 20 comprises a first and second connector slot 26a, 26b for connecting the two corresponding lead connectors 28a, 28b with the two control leads of the spinal cord stimulation paddle (not shown in FIG. 2a). These connector slots 26a, 26b are arranged partially or completely within the antenna 10, i.e. within the projected area formed by the first and second coils 12a, 12b of.

Additionally, the two coils 12a, 12b, the connector slots 26a, 26b, and the corresponding lead connectors 28a, 28b form a sandwich-like structure with the connector slots 26a, 26b and the corresponding lead connectors 28a, 28b disposed in between the two coils 12a, 12b. Especially, the connector slots 26a, 26b are arranged in one of the side surfaces 20d, 20e of the header part 20. This arrangement causes the third coil 12 to be arranged at the opposite side surface 20d, 20e of the side surface 20d, 20e with the connector slots 26a, 26b disposed therein. The two coils 12a, 12b (or optionally the third and/or fourth coils 12) are further connected with the control electronics and the battery 22 (each not shown in FIG. 2a) inside the main housing part 18 via a connection area 30 with feed-throughs serving as a connection interface.

Furthermore, a plurality of connecting wires connecting each terminal of the two lead connectors 28a, 28b to the corresponding pins of the feed-through capacitors of control electronics are also shown in greater detail in FIG. 2a.

FIG. 2b shows a schematic side view of the first embodiment of the antenna 10 together with the implantable pulse generator IPG according to FIG. 1 in more detail.

Especially, the individual windings 14a, 14b of the first and second coil 12a, 12b may be depicted in more detail.

Additionally, a weld 18c in the center of the main housing part 18 is visible therein as the main housing part 18 is built up by welding two housing part shells together.

Additionally, the function of the antenna 10 as shown in FIG. 1 to FIG. 2b together with the implantable pulse generator IPG is as follows:

The antenna 10 for an implantable pulse generator IPG is configured for inductive wireless power transfer and/or near field magnetic induction (NFMI) communication.

Not shown in FIG. 2b is that the inductive wireless power transfer could generally be resonant inductive wireless power transfer.

The antenna 10 for an implantable pulse generator IPG is configured for 6.78 MHz inductive wireless power transfer and for 10.6 MHz near field magnetic induction (NFMI) communication.

In this context, FIG. 3a shows a diagram of a coil coupling coefficient or factor k between the implanted IPG coil 12a,b and the non-implanted device coil of the implanted antenna 10 of the implantable pulse generator IPG according to FIG. 1 to FIG. 2b.

The coil coupling coefficient k is shown between an external and non-implanted coil (e.g. a charging or communication coil) and the implanted antenna 10 of the implantable pulse generator IPG versus a lateral displacement (both linear and in an angular fashion around a round body model) of the antenna 10.

This graph corresponds to a communication use-case, showing (as a dashed horizontal line) the coupling factor k corresponding to the applied receiver sensitivity level, assuming a specific known transmitter output level.

In FIG. 3a, the coupling factor k of the antenna 10 is shown without additional orthogonal coils 12 (e.g. at the side surface 20d, 20e and/or header top surface 20c).

The non-implanted coil for communication is a different one, compared to the used wireless charging coil but one could also use a single coil for both modalities on the external device side.

Figure 3B:
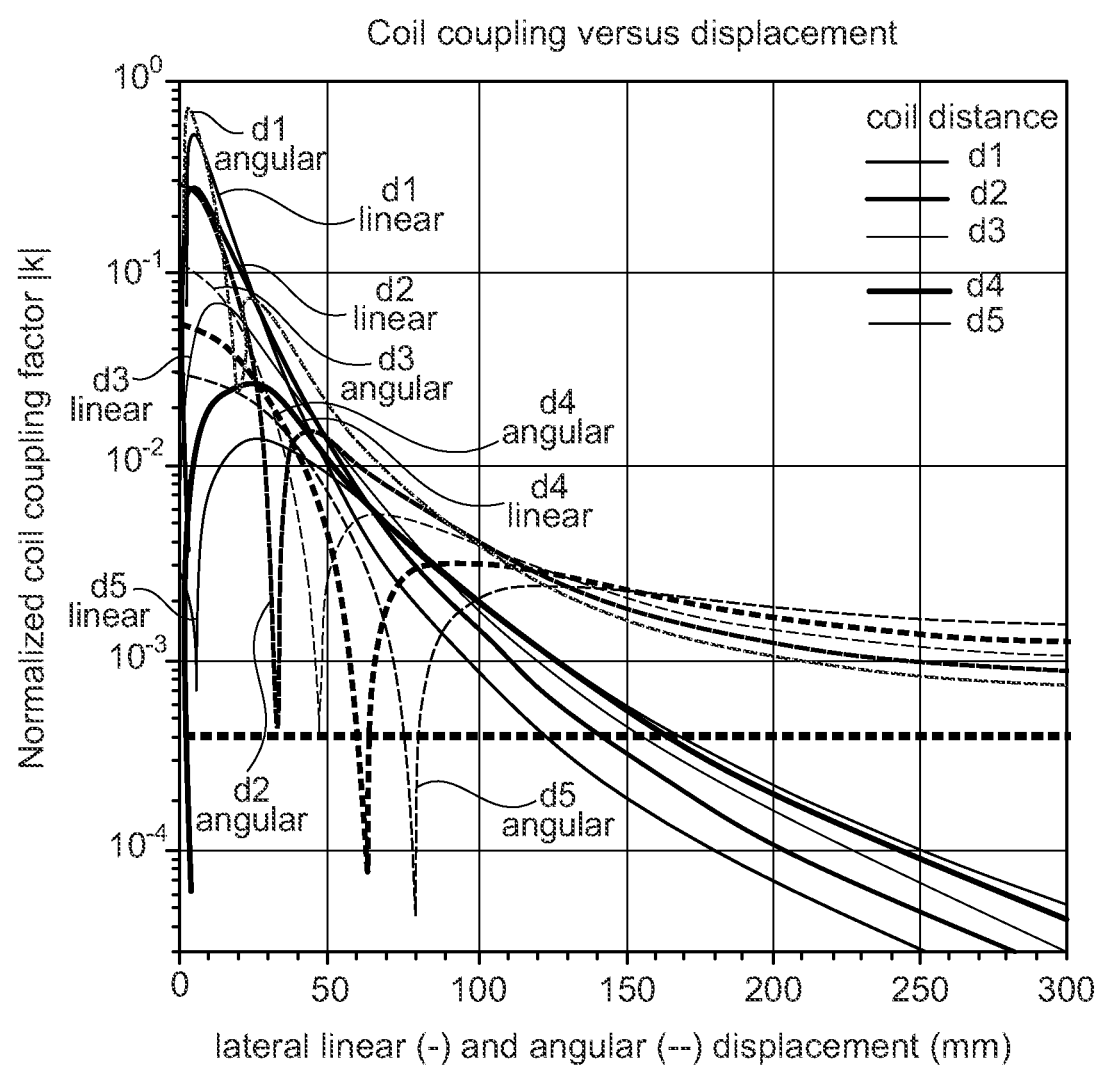
FIG. 3b shows a further diagram of a coil coupling coefficient between the implanted IPG coil and the non-implanted device coil of the implanted antenna of the implantable pulse generator according to FIG. 1.

FIG. 3b shows, in contrast to FIG. 3a, a further diagram of a coil coupling coefficient k between the implanted IPG coil and the non-implanted device coil of the implanted antenna 10 of the implantable pulse generator according to FIG. 1 to FIG. 2b.

Compared to the set up as described in FIG. 3a, the following modifications of the antenna 10 have been implemented:

In contrast to FIG. 3a, FIG. 3b shows the coupling factor k of the antenna 10 with at least one additional orthogonal coil 12 (see FIG. 1, e.g. at the side surface 20d, 20e and/or header top surface 20c), showing an improvement in the k-factor, especially for the angular case (dashed line), leading to a larger communication range. Further, it turns out that the charging performance is not meaningfully impacted by the added orthogonal set(s) of windings in the header 20. Thus, the header antenna 10 (coils 12a, 12b at the main surfaces 20a, 20b) may still be used for both charging and communication.

FIG. 4 shows a schematic view of a mechanical support structure 13 comprised in the header part of the IPG disclosed in FIG. 1. In some embodiments, a mechanical support structure 13 comprising two channel structures 13a, 13b in which each winding 14a, 14b of the two coils 12a, 12b, of the antenna 10 disclosed in FIG. 1 is received and wound around the support structure is shown. The coils 12a, 12b are connected by means of a bridging element 16.

REFERENCES 10 antenna
12 coil
12a coil
12b coil
13 mechanical support structure
13a channel structure
13b channel structure
14 windings
14a windings
14b windings
16 bridging element
18 main housing part
18a planar outer surface
18b planar outer surface
18c weld
20 header part
20a first main surface
20b second main surface
20c header part top surface
20d side surface
20e side surface
22 battery
24 O-Ring
26a connector slot
26b connector slot
28a lead connector
28b lead connector
30 connection area
IMD implantable medical device
IPG implantable pulse generator

The invention claimed is:

1. An antenna for an implantable medical device (IMD), the antenna being configured for inductive wireless power transfer and/or near-field magnetic induction communication, the antenna comprising at least one set of coils and at least one connector interface, wherein the at least one connector interface is configured to receive leads of the IMD and positioned at least partially sandwiched between the coils of the at least one set of coils.

2. The antenna according to claim 1, wherein the inductive wireless power transfer is a resonant inductive wireless power transfer.

3. The antenna according to claim 1 wherein each coil is at least partially made of wire.

4. The antenna according to claim 1, wherein each of the coil of the at least one set of coils is made of a wire with a diameter of 0.05 mm to 0.5 mm.

5. The antenna according to claim 1, wherein the coils of the at least one set of coils comprise an identical number of windings.

6. The antenna according to claim 5, wherein the number of windings is chosen from the range of 1-10 windings.

7. The antenna according to claim 1, wherein the at least one coil forms a rectangular form.

8. An implantable medical device (IMD) comprising at least one antenna according to claim 7.

9. The implantable medical device (IMD) according to claim 8, wherein the implantable medical device (IMD) is an implantable pulse generator (IPG).

10. The implantable medical device (IMD) according to claim 8, wherein the implantable medical device (IMD) has a main housing part and a header part attached to the main housing part, wherein the at least one antenna is arranged in the header part.

11. The implantable medical device (IMD) according to claim 10, wherein the header part is transparent.

12. The implantable medical device (IMD) according to claim 10, wherein the header part is at least partially made of a polymer selected from epoxy, polyurethane, silicone, and combinations thereof.

13. The implantable medical device (IMD) according to claim 8, wherein the coils of the at least one set of coils are arranged in parallel.

14. The implantable medical device (IMD) according to claim 8, wherein the antenna comprises at least one further coil.

15. The implantable medical device (IMD) according to claim 14, wherein the at least one further coil is arranged substantially orthogonally with regard to the at least one set of coils.

16. The implantable medical device (IMD) according to claim 14, wherein the at least one further coil is arranged substantially parallel to the at least one set of coils.

17. The implantable medical device (IMD) according to claim 14, wherein the at least one further coil is arranged substantially at an acute angle with regard to the at least one set of coils.

18. The implantable medical device (IMD) according to claim 8, wherein the header part comprises a mechanical support structure comprising at least one channel structure in which each winding of a coil is received and wound around the support structure.

19. The implantable medical device (IMD) according to claim 8, wherein the implantable medical device (IMD) comprises connector slots arranged at least partially within the at least one antenna.

20. The implantable medical device (IMD) according to claim 8, wherein the implantable medical device (IMD) comprises a switch interface which is configured to decide which coils of the at least one set of coils to use, wherein each coil comprises its own feed-through or is connected to at least one feed-through assigned to it.

* * * * *